United States Patent [19]

Lover

[11] 4,440,763

[45] Apr. 3, 1984

[54] USE OF 4-AMINOSALICYCLIC ACID AS AN ANTI-INFLAMMATORY AGENT

[75] Inventor: Myron J. Lover, Mountainside, N.J.

[73] Assignee: Block Drug Company, Inc., Jersey City, N.J.

[21] Appl. No.: 245,035

[22] Filed: Mar. 18, 1981

[51] Int. Cl.³ .............................................. A61K 31/60
[52] U.S. Cl. ..................................................... 424/230
[58] Field of Search ........................................ 424/230

[56] References Cited

U.S. PATENT DOCUMENTS

| | | | |
|---|---|---|---|
| 2,580,195 | 12/1951 | Rosdahl | 260/525 |
| 2,639,294 | 5/1953 | Rosdahl | 260/519 |
| 2,711,423 | 6/1955 | Smith et al. | 260/519 |
| 2,766,278 | 10/1956 | Grimme et al. | 260/519 |
| 2,874,177 | 2/1959 | Hayano | 260/448 |

FOREIGN PATENT DOCUMENTS 2021409  5/1979  United Kingdom .

OTHER PUBLICATIONS

Helwig "Moderne Arzneimittel", 5th Edition, 1980, pp. 522–524.

*Primary Examiner*—Stanley J. Friedman
*Attorney, Agent, or Firm*—Ostrolenk, Faber, Gerb et al.

[57] ABSTRACT

4-Aminosalicylic acid is used in the treatment of inflammation, e.g., inflammatory bowel disease.

10 Claims, No Drawings

USE OF 4-AMINOSALICYCLIC ACID AS AN ANTI-INFLAMMATORY AGENT

BACKGROUND OF THE INVENTION

Salicylazosulfapyridine (SASP) has been known to be effective in the treatment of ulcerative colitis and has been used clinically for that purpose for over 30 years. When the drug is orally ingested, most reaches the colon intact where it suffers reductive azo-cleavage as a result of action of colonic bacteria to give sulfapyridine (SP) and 5-aminosalicylic acid (5-ASA). SP is abosrbed, distributed throughout the body, and excreted in urine as glucuronide conjugates. Approximately 30% of the 5-ASA is absorbed from the colon, acetylated and excreted in the urine and the remainder is excreted in the feces.

It was determined that the therapeutic mechanism of SASP was primarily a function of the anti-inflammatory 5-ASA and most of the deleterious side effects were associated with SP. Accordingly, 5-ASA has been formulated in a form bound to a suitable polymer for site specific release of 5-ASA in the colon while avoiding the presence of the toxic SP portion of SASP. This is described in Parkinson, et al. U.S. Pat. No. 4,190,716.

5-ASA is unique in that before the present invention, it was the only non-steroidal anti-inflammatory agent known to be useful in the treatment of ulcerative colitis. Other salicylates such as aspirin (acetylsalicylic acid) and other anti-inflammatories such as indomethacin (which is a more potent anti-inflammatory agent) are not effective in the treatment of ulcerative colitis.

4-Aminosalicylic acid (4-ASA) is a well known pharmaceutical agent which has been used for many years in the treatment of tuberculosis. 4-ASA has a bacteriostatic effect on the organism *Mycobacterium tuberculosis* and inhibits the development of bacterial resistance to streptomycin and isoniazid. 4-ASA has invariably been administered as part of a multi-drug regimen including one or both of these drugs.

Even though 4-ASA and 5-ASA are position isomers, they are well recognized to be quite distinct chemically. The salicylic acid backbone is a carboxy-substituted phenol and it is well known that the phenolic hydroxy group or alkoxide ion is a very powerful activator of the benzene ring directing ortho- and para- in electrophylic aromatic substitution. As a result, meta-substituted salicylic acids on one hand, and para- or ortho-substituted salicylic acids on the other hand, are prepared via different processes and undergo different reactions. For example, the meta-substituted 5-ASA is produced by the reduction of a nitro compound by zinc dust and hydrochloric acid or by electrolytic reduction. The para-substituted 4-ASA is prepared by heating 3-aminophenol with ammonium carbonate or potassium bicarbonate under pressure or from the corresponding sodium salt (U.S. Pat. No. 2,844,625). The meta-substituted 5-ASA is very unstable and is known to quickly break down to a dark purple presumed quinone containing tar. The para-substituted 4-ASA also breaks down into a brownish or purplish material but at a much slower rate. Four-ASA, in the presence of moisture readily decarboxylates, whereas 5-ASA does not. Salts of 4-ASA resist decarboxylation. Further, even though 4-ASA has been used for the treatment of millions of tuberculosis patients, there has been no recognition of the anti-inflammatory activity of this compound. Similarly, 5-ASA is not known to be anti-tubercular. Still futher, 4-ASA cannot, because of the steric and activity differences from 5-ASA, be bound to the same polymers as 5-ASA or to other polymers using methods applicable to 5-ASA.

In view of the well recognized distinction chemically between 4-ASA and 5-ASA, it was quite surprising to discover that not only did 4-ASA have anti-inflammatory activity but also it was roughly 50% more potent than 5-ASA. Since the 4-amino compound is more potent and as a salt is also more resistant to degradation, doses which are smaller in absolute amounts can be administered thereby decreasing the magnitude and/or occurence of adverse side effects.

It is accordingly the object of this invention to provide a new anti-inflammatory agent which is useful, interalia, in the treatment of ulcerative colitis and more broadly in inflammatory bowel disease. This and other objects of the invention will become apparent to those skilled in the art from the following detailed disclosure.

SUMMARY OF THE INVENTION

This invention relates to the use of 4-ASA as an anti-inflammatory agent for the treatment of various inflammations including, but not limited to, inflammatory bowel disease, e.g., Crohn's disease and particularly ulcerative colitis.

DESCRIPTION OF THE INVENTION

In accordance with the present invention, 4-ASA can be used as such or in any of its well known pharmaceutically acceptable esters, salts and complexes for the treatment of inflammation. It is useful for the treatment of inflammatory bowel disease, particularly ulcerative colitis. At present, the sodium salt is preferred over the acid since it is more stable than the acid form of the drug. Four-ASA, its esters, salts and complexes are chemical compounds which were commonly used as pharmaceutical agents in the treatment of tuberculosis in man and domestic animals. It can be administered in any of the various forms which have been utilized for 4-ASA heretofore or in the various formulations which SASP or 5-ASA have been used. See, e.g., U.S. Pat. Nos. 2,445,242, 2,540,104, 2,540,785, 2,558,298, 2,580,195, 2,640,854, 2,658,073, 2,844,625, 2,552,486, 2,647,853, 2,667,440, 2,977,281, 2,639,294, 2,655,529, 2,655,532, 2,668,852, 2,711,423, 2,766,278 and 2,874,177. Four-ASA can also be formulated into a "pro-drug", i.e., a compound which breaks down in vivo to liberate the active drug. Preferred administration is orally or topically.

The therapeutically effective doses of 4-ASA are about 60% on a molar basis as the molar dosage effective with SASP or 5-ASA since 4-ASA is about 50% more potent. The recommended daily dosage of SASP is 3–4 g (6–8 tablets) for adult patients and 40–60 mg (divided into 3–4 doses) for pediatric patients. On this basis, a dosage regimen of about 0.5–0.75 g per day divided into 2 or 3 doses can be used. It would be appreciated, however, that the precise amount of the 4-ASA to be administered is best determined by the attending clinician. In the treatment of tuberculosis, the recommended daily dosage of 4-ASA is 10–12 g per os for adults and 200–300 mg/kg for pediatric therapy. It will be appreciated, therefore, that as an anti-inflammatory, greatly reduced amounts of 4-ASA need be administered.

As previously noted, formation of a polymeric bound 5-ASA by the procedure set forth in Parkinson, U.S. Pat. No. 4,190,716 (cannot be directly applied to) 4-ASA because the para-substituted salicylic acid will not bond to the same polymers or through the same bonding reactions. The resulting 5-ASA polymer material does, however, contain a trace amount of 4-ASA. This trace amount has never been recognized as contributing any anti-inflammatory properties to the material and is, in any event, below the pharmaceutically effective threshold of 4-ASA. In adults, such a threshold is in the neighborhood of about 0.2 g per day when administered in a single dose per day and higher in the case of divided daily doses.

A series of animal and clinical studies have been conducted to demonstrate the utility of 4-ASA in the mammilian gastrointestinal tract and to compare it with 5-ASA.

In the animal study, Wistar rats were housed for a period of one week prior to the commencement of testing to determine suitability of each animal and acclimation to the housing environment (2 or 3 rats to a cage in standard suspended cages with wire bottoms). Food and water were available ad libitum. The housing facilities were conditioned for photocycle (12 hours dark/12 hours light) and for temperature (21.4+ or −1.4° C.) and humidity (49+ or −9% RH). The test procedure was based on the carrageenin induced rat paw edema of Winter, et al, Proc. Soc. Exp. Biol. Med. iii, 554–547 (1962) in which each rat was given a sub-plantar injection of 50 ul of a 1% carrageenin in saline solution (positive control) or saline (negative control) in a paw whose volume had been previously determined. In the test groups, each rat was given an intraperitoneal injection of 10 mg/kg of 4-ASA or 5-ASA or phenylbutazone prior to challenge with the carrageenin suspension. At 3, 5 and 7 hours after treatment with carrageenin or saline, the volume of each treated paw was measured.

| Treatment Group | Mean* Paw Edema in ml. Time of reading (hours after carragennin or saline injection) | | |
|---|---|---|---|
| | 3 | 5 | 7 |
| Carrageenin Control | 0.482 | 0.575 | 0.420 |
| Saline Control | 0.082 | 0.098 | 0.086 |
| Carrageenin and 4-ASA | 0.257 | 0.265 | 0.238 |
| Carrageenin and 5-ASA | 0.379 | 0.379 | 0.255 |
| Carrageenin and phenylbutazone | 0.345 | 0.362 | 0.284 |

*10 paws

The foregoing data show that phenylbutazone and 5-ASA are of a similar order of activity at the dose levels tested while 4-ASA has a significantly greater anti-inflammatory activity.

In the clinical study, eight volunteers with proven ulcerative colitis and not receiving oral corticosteriods or azathioprine were given either an enema containing 1 g of 4-ASA sodium salt or a control enema nightly. The study was conducted on a double blind basis. The four patients receiving the 4-ASA sodium salt responded well clinically and of the four patients receiving the placebo, three had no clinical response and one had a slight clinical response.

Various changes and modifications can be made in the process of the present invention without departing from the spirit and scope thereof. The various embodiments which have been disclosed herein were for the purpose of further illustrating the invention but were not intended to limit it.

An enema precursor composition can be prepared by dry blending the 4-ASA* with carriers and packaging unit doses. Each unit can contain Na 4-ASA 2 g, lactose 3.5 g, colloidal $SiO_2$ 0.005 g, carboxymethylcellulose Na 0.2 g and Na starch glycolate 0.05 g. The enema is prepared by mixing the contents of the package with water q.s. 100 ml immediately before use.
* 4-Aminosalicylic acid

What is claimed is:

1. A method of treating inflammation which comprises administering to a mammal having an inflammatory condition an anti-inflammatory effective amount of a composition consisting essentially of 4-aminosalicylic acid or a pharmaceutically acceptable ester, salt, prodrug or complex thereof.

2. The method of claim 1 wherein said inflammation is in the gastrointestinal tract.

3. The method of claim 2 wherein said inflammation is inflammatory bowel disease.

4. The method of claim 3 wherein said inflammatory bowel disease is ulcerative colitis.

5. The method of claim 1 or 4 wherein said 4-aminosalicylic acid is employed in the form of its sodium salt.

6. The method of claim 5 wherein said anti-inflammatory effective amount is at least about 0.2 g per day.

7. The method of claim 1 wherein said anti-inflammatory effective amount is at least about 0.2 g per day.

8. The method of claim 1 wherein said administration is oral.

9. The method of claim 1 wherein said administration is topical.

10. The method of claims 1 and 9, where the topical administration is intra-rectal.

* * * * *